(12) United States Patent
Razifar et al.

(10) Patent No.: US 8,233,689 B2
(45) Date of Patent: Jul. 31, 2012

(54) METHOD AND SYSTEM OF MULTIVARIATE ANALYSIS ON VOLUME-WISE DATA OF REFERENCE STRUCTURE NORMALIZED IMAGES FOR IMPROVED QUALITY IN POSITRON EMISSION TOMOGRAPHY STUDIES

(75) Inventors: Pasha Razifar, Uppsala (SE); Mats Bergstrom, London (GB); Bengt Langstrom, Uppsala (SE)

(73) Assignee: GE Healthcare Limited, Buckinghamshire (GB)

( * ) Notice: Subject to any disclaimer, the term of this patent is extended or adjusted under 35 U.S.C. 154(b) by 960 days.

(21) Appl. No.: 12/065,119

(22) PCT Filed: Aug. 31, 2006

(86) PCT No.: PCT/IB2006/002390
§ 371 (c)(1),
(2), (4) Date: Jul. 14, 2008

(87) PCT Pub. No.: WO2007/026231
PCT Pub. Date: Mar. 8, 2007

(65) Prior Publication Data
US 2008/0279436 A1    Nov. 13, 2008

Related U.S. Application Data

(60) Provisional application No. 60/712,784, filed on Aug. 31, 2005.

(51) Int. Cl.
*G06K 9/00* (2006.01)
(52) U.S. Cl. ........................................................ 382/131
(58) Field of Classification Search .......... 382/128–132, 382/171, 181, 190, 224, 254, 275
See application file for complete search history.

(56) References Cited

PUBLICATIONS

Pedersen, F, et al. (1995) "An extended strategy for exploratory multivariate image analysis includimg noise considerations" Journal of Chemometrics, vol. 9, pp. 389-409.*
Bengtsson, E, et al. (1994) "MUSE—new tool for interactive image analysis and segmentation based on multivariate statistics" Computer Methods and Programs in Biomedicine vol. 42m pp. 181-200.*
Pedersen, F. et.al. "An extended strategy for exploratory multivariate image analysis including noise considerations" Journal of Chemometrics, Wiley, Chichester, Sussex, England GB, vol. 9, No. 5 Oct. 1995 pp. 389-409.
Bengtsson, Ewert, et.al. "MUSE—new tool for interactive image analysis and segmentation based on multivariate statistics" Computer Methods and Programs in Biomedicine, vol. 42, No. 3, Mar. 1994 pp. 181-200.
Samal, M, et.al. "Experimental comparison of data transformation procedures for analysis of principal components" Physics in Medicine and Biology, Taylor and Francis Ltd., London GB, vol. 44, No. 11, Nov. 1999 pp. 2821-2834.
PCT/IB2006/002390 Int'l search report/written opinion dated Aug. 2007.
* cited by examiner

*Primary Examiner* — Courtney Thomas
(74) *Attorney, Agent, or Firm* — Robert F. Chisholm

(57) ABSTRACT

A method and system are provided to mask out the background in dynamic PET images, to perform pre-normalization on the masked dynamic PET images, and to apply multivariate image analysis (e.g., principal component analysis PCA) on the masked pre-normalized dynamic PET images in order to improve the quality of the dynamic PET images and the PET study. A masking operation applies PCA to untreated dynamic PEET images before any pre-normalization in order to mask out the background pixels. This masking operation uses the Otsu method. A first normalization method is background noise pre-normalization where pixel values are corrected for background noise. A second normalization method is kinetic pre-normalization where the contrast within an image is improved. Multivariate analysis such as PCA may be applied on the whole volume to find the largest variance in the structure.

12 Claims, 12 Drawing Sheets

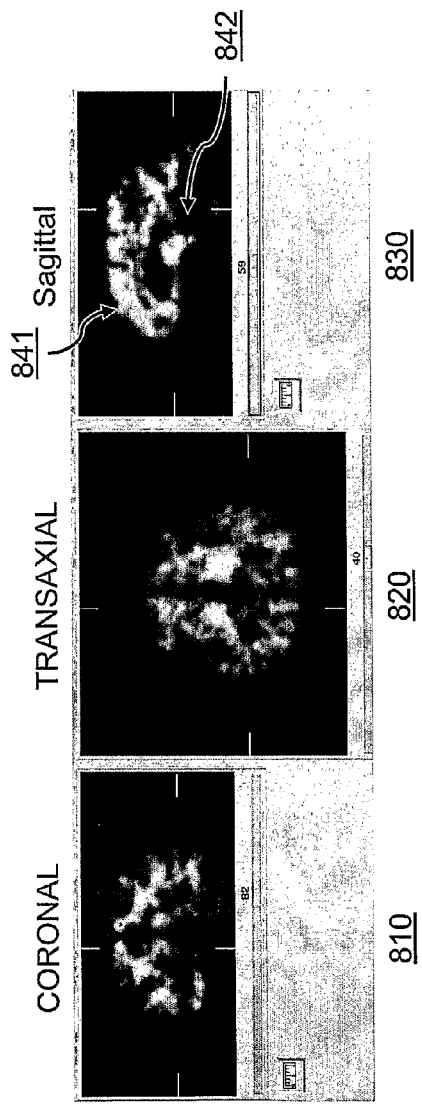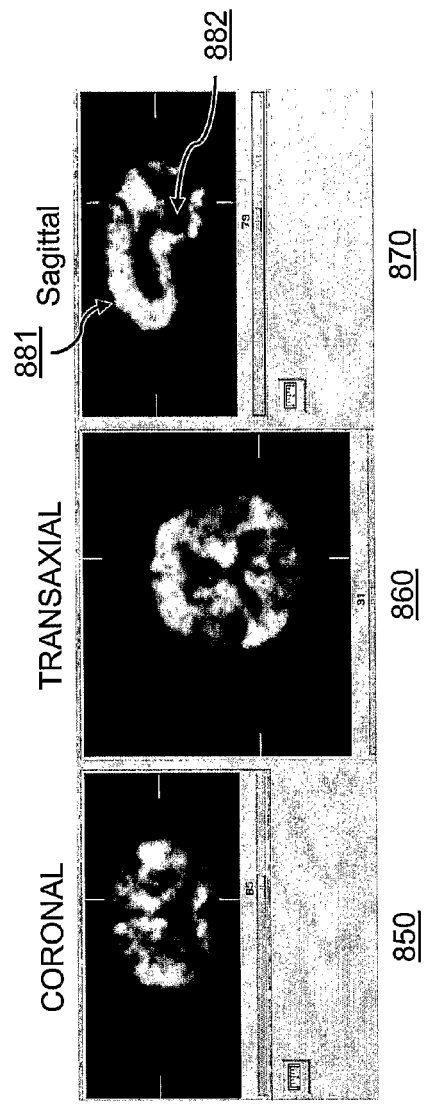
FIG. 8A
FIG. 8B

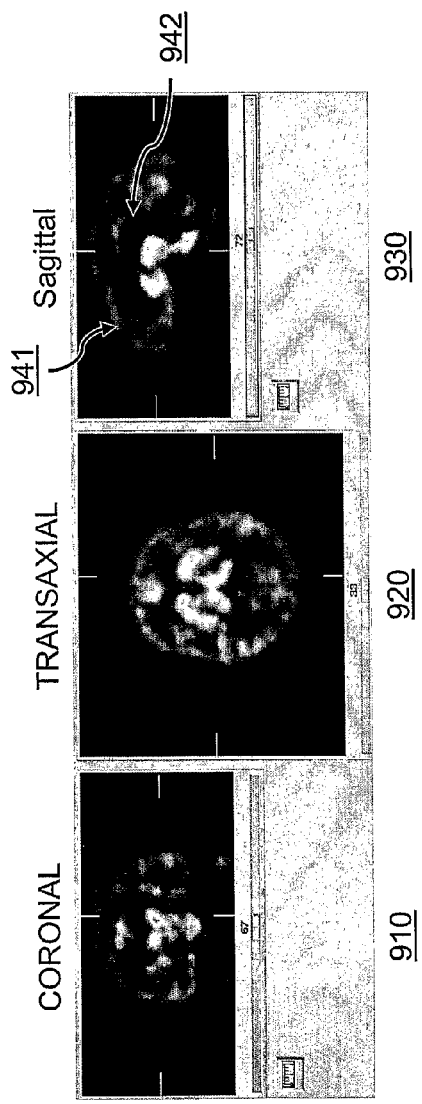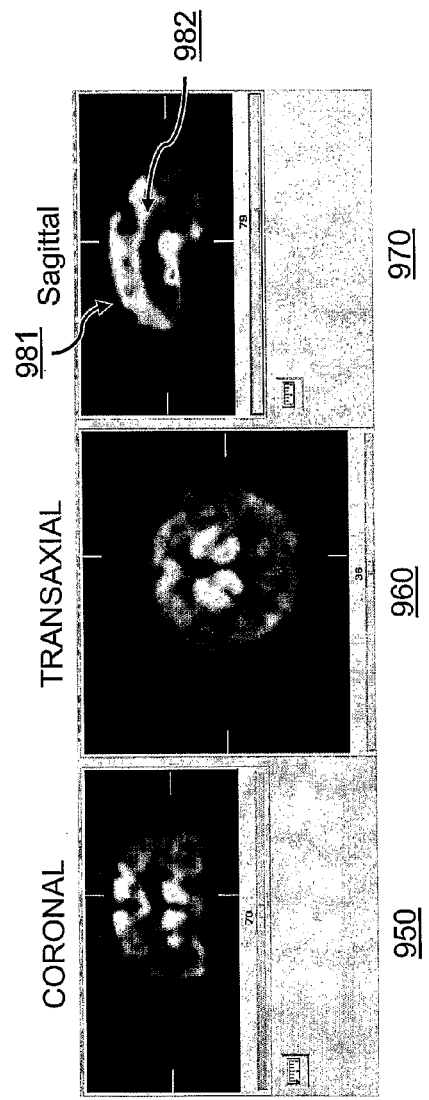
FIG.9A
FIG.9B

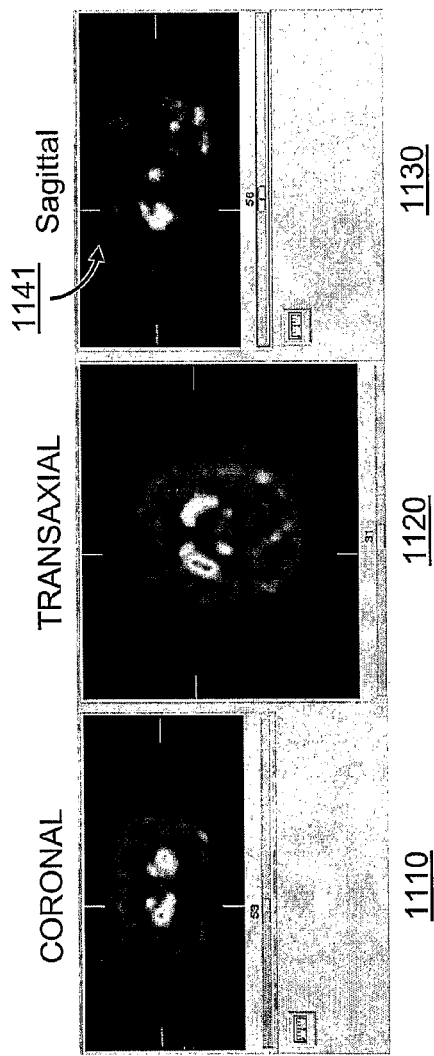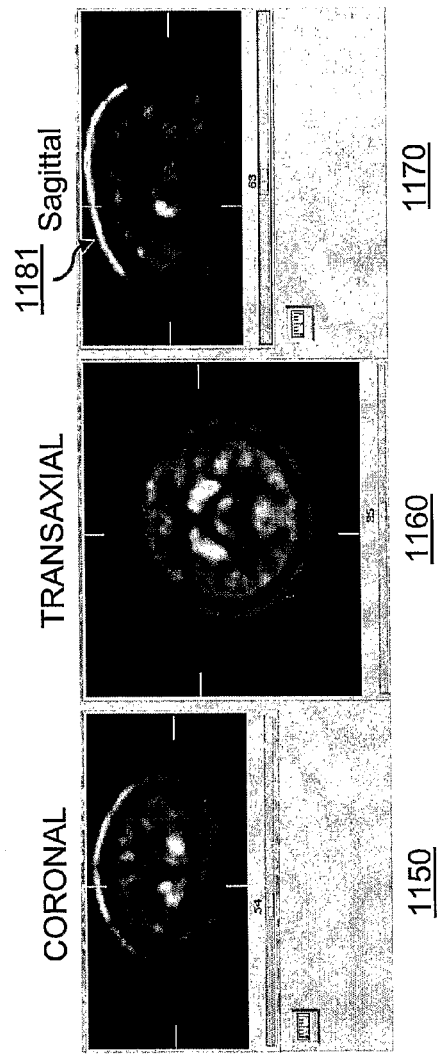

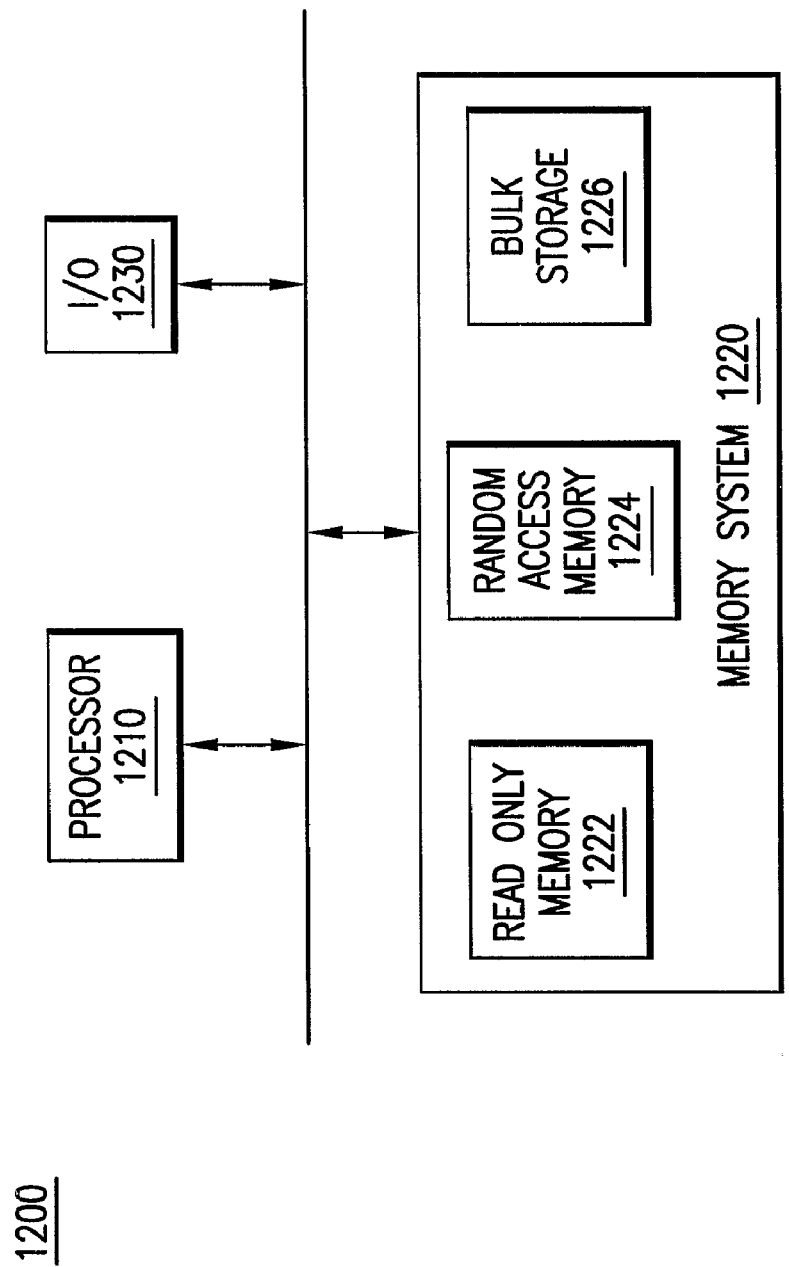

METHOD AND SYSTEM OF MULTIVARIATE ANALYSIS ON VOLUME-WISE DATA OF REFERENCE STRUCTURE NORMALIZED IMAGES FOR IMPROVED QUALITY IN POSITRON EMISSION TOMOGRAPHY STUDIES

This application is a filing under 35 U.S.C. 371 of international application number PCT/IB2006/002390, filed Aug. 31, 2006, which claims priority to application No. 60/712,784 filed Aug. 31, 2005, in the United States the entire disclosure of which is hereby incorporated by reference.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

The present invention relates to a method and system of multivariate analysis of reference structure normalized images for improved quality in positron emission tomography (PET) studies. One embodiment of the present invention relates to the use of principal component analysis (PCA) as the multivariate analysis tool. This embodiment further relates to the application of PCA on volume-wise dynamic PET images which may involve masking out the background data and using pre-normalization techniques to reduce or factor out background noise and/or to enhance contrast.

BACKGROUND

Positron Emission Tomography (PET) is an available specialized imaging technique that uses tomography to computer-generate a three-dimensional image or map of a functional process in the body as a result of detecting gamma rays when artificially introduced radionuclides incorporated into biochemical substances decay and release positrons. Analysis of the photons detected from the deterioration of these positrons is used to generate the tomographic images which may be quantified using a color scale to show the diffusion of the biochemical substances in the tissue indicating localization of metabolic and/or physiological processes. For example, radionuclides used in PET may be a short-lived radioactive isotope such as Flourine-18, Oxygen-15, Nitrogen-13, and Carbon-11 (with half-lives ranging from 110 minutes to 20 minutes). The radionuclides may be incorporated into biochemical substances such as compounds normally used by the body that may include, for example, sugars, water, and/or ammonia. The biochemical substances may then be injected or inhaled into the body (e.g., into the blood stream) where the substance (e.g., a sugar) becomes concentrated in the tissue of interest where the radionuclides begin to decay emitting a positron. The positron collides with an electron producing gamma ray photons which can be detected and recorded indicating where the radionuclide was taken up into the body. This set of data may be used to explore and depict anatomical, physiological, and metabolic information in the human body. While alternative scanning methods such as Magnetic Resonance Imaging (MRI), Functional Magnetic Resonance Imaging (fMRI), Computed Tomography (CT), and Single Photon Emission Computed Tomography (SPECT) may be used to isolate anatomic changes in the body, PET may use administrated radiolabeled molecules to detect molecular detail even prior to anatomic change.

PET studies in humans are typically performed in either one of two modes, providing different sets of data: whole body acquisition whereby static data for one body sector at a time is sequentially recorded and dynamic acquisition whereby the same sector is sequentially imaged at different time points or frames. Dynamic PET studies collect and generate data sets in the form of congruent images obtained from the same sector. These sequential images can be regarded as multivariate images from which physiological, biochemical and functional information can be derived by analyzing the distribution and kinetics of administrated radiolabeled molecules. Each one of the images in the sequence displays/contains part of the kinetic information.

Due to limitations in the amount of radioactivity administered to the subject, a usually short half-life of the radionuclide and limited sensitivity of the recording system, dynamic PET images are typically characterized by a rather high level of noise. This together with a high level of non-specific binding to the target and sometimes small differences in target expression between healthy and pathological areas are factors which make the analysis of dynamic PET images difficult independent of the utilized radionuclide or type of experiment. This means that the individual images are not optimal for the analysis and visualization of anatomy and pathology. One of the standard methods used for the reduction of the noise and quantitative estimation in dynamic PET images is to take the sum, average, or mean of the images of the whole sequence or part of the sequence where the specific signal is proportionally larger. However, though sum, average, or mean images may be effective in reducing noise, these approaches result in the dampening of the differences detected between regions with different kinetic behavior.

Another method used for analysis of dynamic PET images is kinetic modeling with the generation of parametric images, aiming to extract areas with specific kinetic properties that can enhance the discrimination between normal and pathologic regions. One of the well established kinetic modeling methods used for parameter estimation is known as the Patlak method (or sometimes Gjedde method). The ratio of target region to reference radioactivity concentration is plotted against a modified time, obtained as the time integral of the reference radioactivity concentration up to the selected time divided by the radioactivity concentration at this time. In cases where the tracer accumulation can be described as irreversible, the Patlak graphical representation of tracer kinetics becomes a straight line with a slope proportional to the accumulation rate. This method can readily be applied to each pixel separately in a dynamic imaging sequence and allows the generation of parametric images representative of the accumulation rate. Alternative methods for the generation of parametric images exist; based on other types of modeling, e.g. Logan plots, compartment modeling, or extraction of components such as in factor analysis or spectral analysis. Other alternatives such as population approaches, where an iterative two stage (ITS) method is utilized, have been proposed and studied and are available.

A notable problem when using kinetic modeling is that the generated parametric images suffer from poor quality while the images are rather noisy. This indicates that kinetic modeling methods such as Reference Patlak, do not consider any Signal-to-Noise-Ratio (SNR) optimization during the measurement of physiological parameters from dynamic data.

Dynamic PET images can also be analyzed utilizing different multivariate, statistical techniques such as Principal Component Analysis (PCA), which is one of the most commonly used multivariate analysis tools. PCA also has several other applications in the medical imaging field such as, for example, in Computed Tomography (CT) and in functional Magnetic Resonance Imaging (fMRI). This technique is employed in order to find variance-covariance structures of the input data in unison to reduce the dimensionality of the data set. The results of the PCA can further be used for different purposes e.g. factor analysis, regression analysis, and used for performing preprocessing of the input/raw data.

The conventional use of PCA indicates a data driven technique which has difficulty in separating the signal from the noise when the magnitude of the noise is relatively high. The presence of variable noise levels in the different PET images dramatically affects the subsequent multivariate analysis unless properly handled otherwise PCA will emphasize noise and not the regions with different kinetics. For this reason, using PCA on dynamic PET images is not an optimal solution.

BRIEF DESCRIPTION OF THE DRAWINGS

FIG. 8a is a selection of first principal component images taken from different perspectives or planes generated by applying the MVW-PCA method on dynamic PET images according to one embodiment of the present invention in a PET study of the human brain in a healthy volunteer using a Pittsburgh Compound-B (PIB) tracer.

FIG. 8b is a selection of first principal component images taken from different perspectives or planes generated by applying the MVW-PCA method on dynamic PET images according to one embodiment of the present invention in a PET study of the human brain in a patient with Alzheimer's disease using a Pittsburgh Compound-B (PIB) tracer.

FIG. 9a is a selection of first principal component images taken from different perspectives or planes generated by applying the MVW-PCA method on dynamic PET images according to one embodiment of the present invention in a PET study of the human brain in a healthy volunteer using an $[^{11}C]$-L-deuterium-deprenyl (DED) tracer.

FIG. 9b is a selection of first principal component images taken from different perspectives or planes generated by applying the MVW-PCA method on dynamic PET images according to one embodiment of the present invention in a PET study of the human brain in a patient with Alzheimer's disease using an $[^{11}C]$-L-deuterium-deprenyl (DED) tracer.

FIG. 11a is a selection of first principal component images taken from different perspectives or planes generated by applying the MVW-PCA method on dynamic PET images according to one embodiment of the present invention in a PET study of the human brain in a healthy volunteer using an $[^{11}C]$-L-DOPA (DOPA) tracer.

FIG. 11b is a selection of first principal component images taken from different perspectives or planes generated by applying the MVW-PCA method on dynamic PET images according to one embodiment of the present invention in a PET study of the human brain in a patient with chronic fatigue syndrome (CFS) using an $[^{11}C]$-L-DOPA (DOPA) tracer.

FIG. 12 is a block diagram illustrating the platform on which the MVW-PCA method for applying PCA to dynamic PET images using pre-normalization techniques may operate according to one embodiment of the present invention.

DETAILED DESCRIPTION

Figure 1:
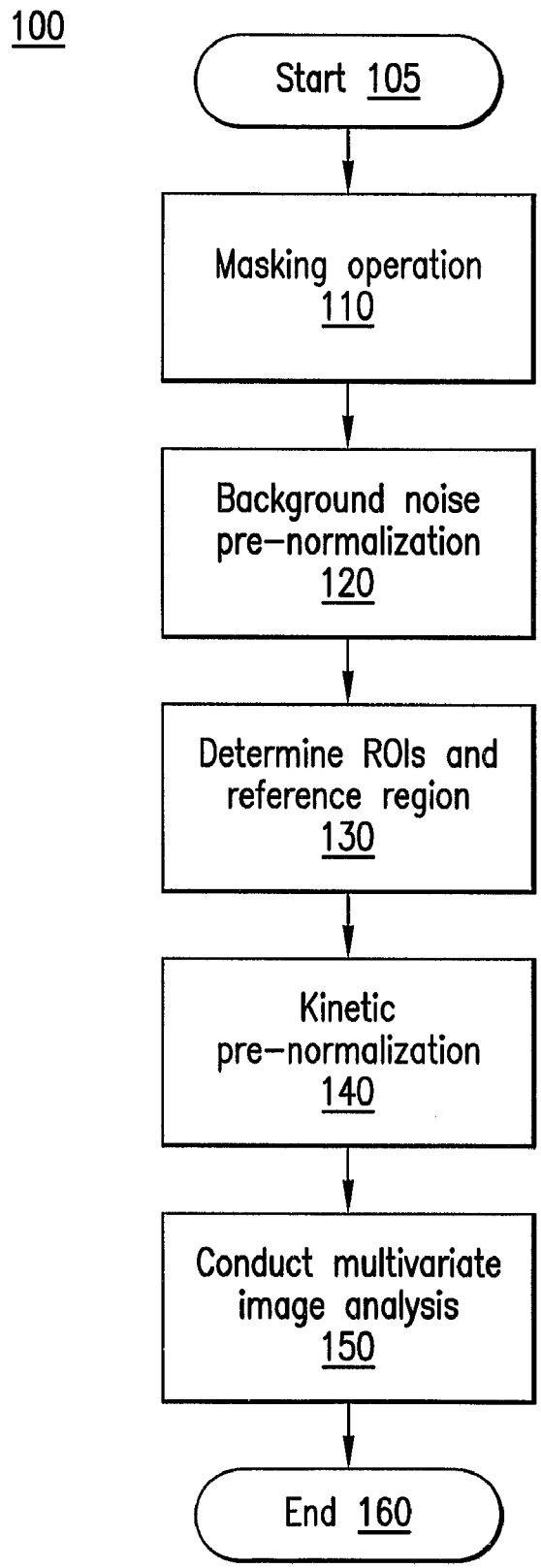
FIG. 1 is a flowchart illustrating one method or process for improving PET image quality according to one embodiment of the present invention.

In one embodiment of the present invention, these limitations are at least partially overcome by a method and system of masking out the background in the dynamic PET images, performing pre-normalization on the masked dynamic PET images, and applying multivariate image analysis (e.g., principal component analysis—PCA) on the masked pre-normalized dynamic PET images in order to improve discrimination between affected and unaffected regions in the brain and improving the quality of the PET images and diagnosis in the PET studies. The dynamic PET images (i.e., also referred to herein as reconstructed dynamic PET data or reconstructed PET data) are the images reconstructed from the raw dynamic PET data in the image domain of the PET study. A masking operation according to one embodiment of the present invention applies PCA to the untreated dynamic PET images before any pre-normalization in order to generate a first principal component (PC1 image) used to distinguish an object (e.g., a brain) from the background in order to mask out the background pixels. This masking operation according to this embodiment uses the Otsu method to determine a threshold value used in an automated masking procedure. A first normalization method for the masked dynamic PET input data according to one embodiment is a background noise pre-normalization where the pixel values are corrected for background noise in the image. A second normalization method according to one embodiment is a kinetic pre-normalization (i.e., a contrast enhancement procedure) where the contrast between affected and unaffected regions of the brain (the object) within an image is improved to allow greater visualization of the activity in the image. This normalization of the dynamic PET images is termed pre-normalization herein because it occurs prior to the main processing which in this case is the multivariate analysis (e.g., PCA). In alternative embodiments of the present invention, both the preceding pre-normalization methods may be performed in reverse order, only one of the pre-normalization methods performed, or none of the pre-normalization method may be used. In one example embodiment of the present invention, both pre-normalization methods are applied. Multivariate analysis using a tool such as PCA may be applied according to one embodiment of the present invention on the masked pre-normalized dynamic PET images (i.e., the masked pre-normalized PET images). Additionally, the whole volume (i.e., volume-wise application of PCA) may be used rather the slice-wise application of PCA to further improve the quality of the PET images by forcing the PCA to analyze the whole volume at one time thereby finding and using the largest variance in the volume-wise structure. This masked volume-wise application of PCA (MVW-PCA) according to this embodiment may significantly improve the quality of the images in a positron emission tomography (PET) study.

According to one embodiment of the present invention, data enhancement techniques (i.e., the masking operation and the pre-normalization methods) and multivariate analysis may be used on the dynamic PET images to enhance the quality of the PET study using a whole volume approach on a biological and/or anatomical region or process in the body (such as for example in the human brain). Even though this embodiment is discussed in relation to using conventional tracers (administrated radiolabeled molecules) in different clinical applications on the human brain, other embodiments of the present invention may be applied to other biological and/or anatomical regions and/or processes in a human or other body or in other PET applications. The data enhancement techniques discussed herein may be used individually or in combination with each other and in conjunction with multivariate analysis (such as for example principal component analysis—PCA). The embodiments discussed herein refer to principal component analysis (PCA) as the multivariate analysis tool though other tools such as independent component analysis (ICA) may alternatively be used.

FIG. 1 is a flowchart illustrating one method or process for improving PET image quality according to one embodiment of the present invention. The process 100 begins 105 by performing a masking operation 110 on the background pixels in the dynamic PET image. This masking operation 110 may be followed by background noise pre-normalization 120. Background noise pre-normalization 120 may involve estimating the standard deviation of the noise in the background area of the image. The background area may be determined during the masking operation 110. This background noise pre-normalization may be performed on the whole volume that is for each slice through all the frames (i.e., all the frames or time periods for a particular plane or slice) or may alternatively be performed separately for each slice and frame. Either way, the masked dynamic PET input data is adjusted accordingly. After background noise pre-normalization 120, a Region of Interest (ROI) is drawn for an outlined region of the object under study (e.g., the brain) 130. Kinetic pre-normalization 140 (which may also be referred to herein as biological pre-normalization or contrast enhancement) may then be performed. Kinetic pre-normalization 140 involves taking all the slices (i.e. images taken from different perspectives and/or covering different biological or anatomical areas or planes) for each frame (i.e., period of time or snapshot in time) and dividing by the mean value within the selected ROI(s) representing a reference region (e.g., a region of the brain that is devoid of specific binding and is representative of the free tracer fraction in the target tissue) within the frame in order to enhance the contrast and margin between affected and unaffected regions within the images. The masking operation 110 and these pre-normalization methods 120, 130, 140 allow for the enhanced performance of a multivariate image analysis tool 150, such as PCA, on the dynamic PET image before the process concludes 160. The simplified flowchart shown in FIG. 1 outlines only one method or process for improving PET image quality according to one embodiment of the present invention. This overall process and the associated masking operation and pre-normalization methods are discussed in greater detail below.

The first step in the Masked Volume-Wise application of PCA (MVW-PCA) is the masking operation 110 where the background pixels are masked out and PCA is applied using the whole, masked biological or anatomical region such as, for example, the brain in order to avoid the influence of a low signal from the areas outside the region. Using the brain as an example of an anatomical region, a mask is applied so that the signal for areas outside the brain is excluded from the PCA analysis. A threshold value may be used in applying the mask. However, extracranial tissues may also be included in the masked data in this example embodiment by applying a threshold value to visualize the brain as discussed below.

Figure 2:
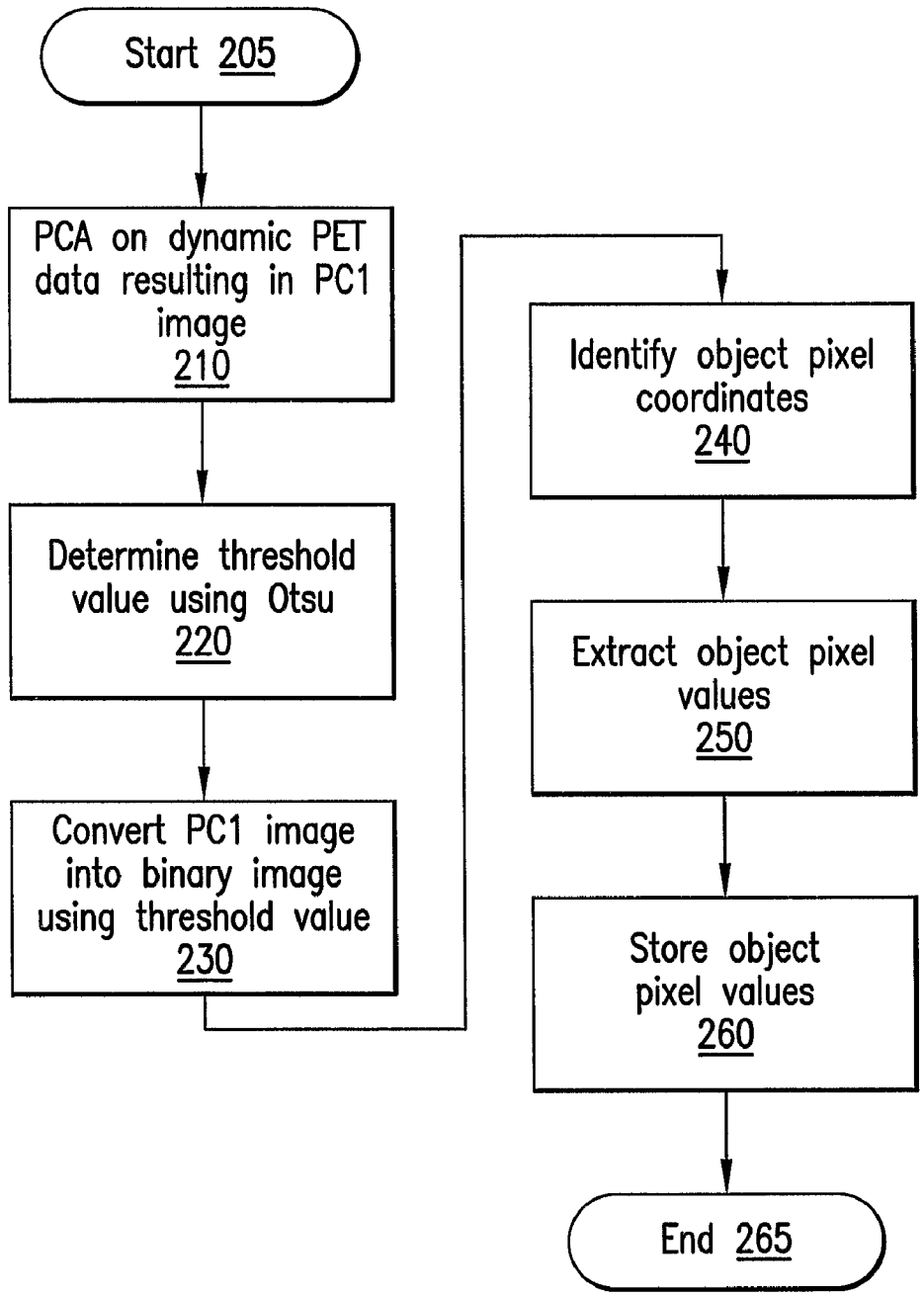
FIG. 2 is a flowchart illustrating the masking operation used in the Masked Volume-Wise application of PCA (MVW-PCA) according to one embodiment of the present invention.

FIG. 2 is a flowchart illustrating the masking operation used in the Masked Volume-Wise application of PCA (MVW-PCA) according to one embodiment of the present invention. The masking operation 200 begins 205 using the dynamic PET images before any pre-normalization operation is performed. In a first step 210, PCA is performed on these untreated dynamic PET images resulting in a first principal component image (i.e., a PC1 image) for each slice in the PET study (one PC1 image is generated for all the frames of each slice). A threshold value for the masking operation may be determined 220 using the available Otsu method (though the Otsu method is available it is not generally used with dynamic PET images) to iteratively determine a global threshold value. In this embodiment, the masking is performed slice-wise where a global threshold value is determined for all frames for each slice. In alternative embodiments of the present invention, other methods rather than the Otsu method may be used to determine this threshold value. Additionally, the determination of the threshold value may occur elsewhere in the process in an alternative embodiment. The PC1 images are then converted 230 in a third step into binary images where each of the pixels is given a value of either, for example, one for an object pixel (i.e., a pixel representing the object under study such as the brain) and zero for a background pixel based on the masking determination using the threshold value. Coordinates for the object pixels (within the contours of the object) in all the PC1 images are then saved 240. The corresponding object pixels are extracted 250 from each of the slices for the PC1 image using these coordinates and the pixel values are stored 260 in a column vector (e.g., k=1, 2, 3, ..., 63) of a matrix (e.g., $C_{kl}$) containing all the pixels from the PC1 image for the different frames (e.g., l=1, 2, 3, ..., N where N is the number of frames). The completion 265 of the masking operation 200 results in a new input matrix $C_{kl}$ containing the masked object data which then serves as the new set of masked input data for the MVW-PCA.

This new input matrix may then be used for background noise pre-normalization in order to improve the performance of the multivariate analysis (e.g., PCA) that will be conducted as part of the MVW-PCA process according to one embodiment of the present invention. Background noise pre-normalization (also referred to herein as "nor1" pre-normalization) is the second step 120 in the process 100 shown in FIG. 1. According to one embodiment, each pixel value j in an image i may be divided by the standard deviation $s_i$ of the noise calculated from an outlined masked area in the background of the image represented by a vector containing these masked background pixel values in order to normalize the pixel values to factor out or reduce the background noise in the image. This may be shown in the equation below where $x_{ij}$ refers to the original value of the pixel j of image i and $X_{ij}$ refers to the resulting new value for the pixel.

$$X_{ij} = x_{ij}/S_i$$

This equation may be applied to all the pixels in an image according to this embodiment of the present invention. Pixels with a value of zero will of course retain their zero value even if this equation is applied and, therefore, this equation may be selectively applied to pixels containing a non-zero value in an alternative embodiment.

A third step 130 in the process 100 is to identify at least one region of interest (ROI) for the whole brain (i.e., object under study) (which may include a reference region that is devoid of specific binding such as, for example, the cerebellum) and then to use the ROI(s) in a fourth step 140 to improve the contrast between affected and unaffected regions in the image according to this embodiment. The contrast of a PET image may be improved thereby allowing a greater visualization of the activity in the PET image according to one embodiment of the present invention. According to this embodiment, kinetic pre-normalization (i.e., contrast enhancement) may be performed using ROI(s) representing the reference region in order to improve the contrast within the PET image (also referred to herein as "mixp" pre-normalization). The reference region may be determined 130 by outlining the regions-of-interest (ROI) for a region devoid of specific binding and representative of the free tracer fraction in the target tissue for the biological or anatomical area being studied (such as, for example, a cerebellar cortex). ROI representing the reference region can be outlined on images obtained from either applying PCA on non-pre-normalized images or, for example, using sum images. In other words, principal component analysis (PCA) may be performed on the frames for a PET study without first performing any background noise pre-normalization. This may, for example, result in a first principal component for a single frame containing a corresponding number of planes/slices (e.g., 63) with improved contrast (for example, particularly between the white and gray matter in a cerebellar cortex) allowing greater visualization of the biological or anatomical area being studied and displaying an improved signal-to-noise ration (SNR). The reference region may then be determined from the ROI(s) identified through this process in one embodiment of the present invention. Other alternative embodiments may determine the reference region differently (for example, using sum images).

Kinetic pre-normalization according to one embodiment of the present invention is performed by dividing the value of each pixel j in a single image i by the mean value $\bar{x}_i$ of the pixels within the reference region as determined by the ROI(s) as discussed above. This kinetic pre-normalization equation according to this embodiment is shown below.

$$X_{ij} = X_{ij}/\bar{x}_i$$

Kinetic pre-normalization improves the contrast between different regions in the PET images by reducing the pixel values according the kinetic behavior of the reference region. The equation above is one embodiment of this method for aiding in the improved visualization of the kinetic activity in the PET images. Kinetic pre-normalization according to this embodiment is based on dividing each pixel in an image in each frame by the mean value of the pixels within the drawn ROI(s) representing a reference region (such as, for example, the cerebellar cortex) that is devoid of specific binding. In one embodiment, the drawing of the ROI(s) representing the reference region may be performed manually by a user. In an alternative embodiment, this process may be partially or fully automated by, for example, allowing a user to select a region on an image with automated software determining the region boundaries. The masking operation 110, background noise pre-normalization 120, determining the ROI(s) and the reference region 130, and kinetic pre-normalization 140 are preparatory pre-normalization steps for the multivariate analysis tool (e.g., PCA) in one embodiment of the MVW-PCA method.

PCA is a well-established technique based on exploring the variance-covariance or correlation structure between the input data represented in different Principal Components (PCs). PCA is based on the transformation of the original data in order to reduce the dimensionality by calculating transformation vectors (PCs), which define the directions of maximum variance of the data in the multidimensional feature space. Each PC is orthogonal to all the others meaning that the first PC (e.g., PC1) represents the linear combination of the original variables containing the maximum variance, the second PC (e.g., PC2) is the combination containing as much of the remaining variance as possible orthogonal to the previous PC (e.g., PC1) and so on. The term "PC images" corresponds to "Score images" and are used in conjunction with performing back projection of data and visualization of the PC vectors as images.

In one embodiment of the present invention, MVW-PCA can be further refined by using conventionally utilized tracers (administered radiolabeled molecules) in different clinical applications for a biological or anatomical region such as, for example, the human brain as previously discussed. According to this embodiment, using the whole brain (WB) or volume-wise (VW) data (i.e., all data for a frame rather than by slice or plane) instead of slice-wise data from each frame (a slice exists in the image domain and there may be multiple slices per frame) may result in the PCA being forced to determine the largest variance within the whole brain (volume-wise) containing all structures at the same time. This may be advantageous over applying slice-wise PCA (SW-PCA) on dynamic PET images which generates results in which each slice of the brain is treated separately and independently from other slices of the brain in the same frame. Using the whole brain (volume-wise) data over slice-wise data may avoid the potential problem where quantitative values of the principal component (PC) images differ between the slices which may result in a streaky image appearance when generating sagittal and/or coronal images from the PC images when slice-wise data is used. Performing PCA on the whole brain (volume-wise) involves analysis on all parts of the studied structure (i.e., the brain) at one time where the PCA is forced to determine the maximum variance of the input data from an input matrix (e.g., the new masked input data previously discussed) containing data from the whole brain but for different frames for the whole brain (the whole brain information is taken together but separately analyzed for each frame). Though described for the brain in this embodiment, MVW-PCA may be applied to other anatomical and/or biological regions in alternative embodiments of the present invention.

Figure 3:
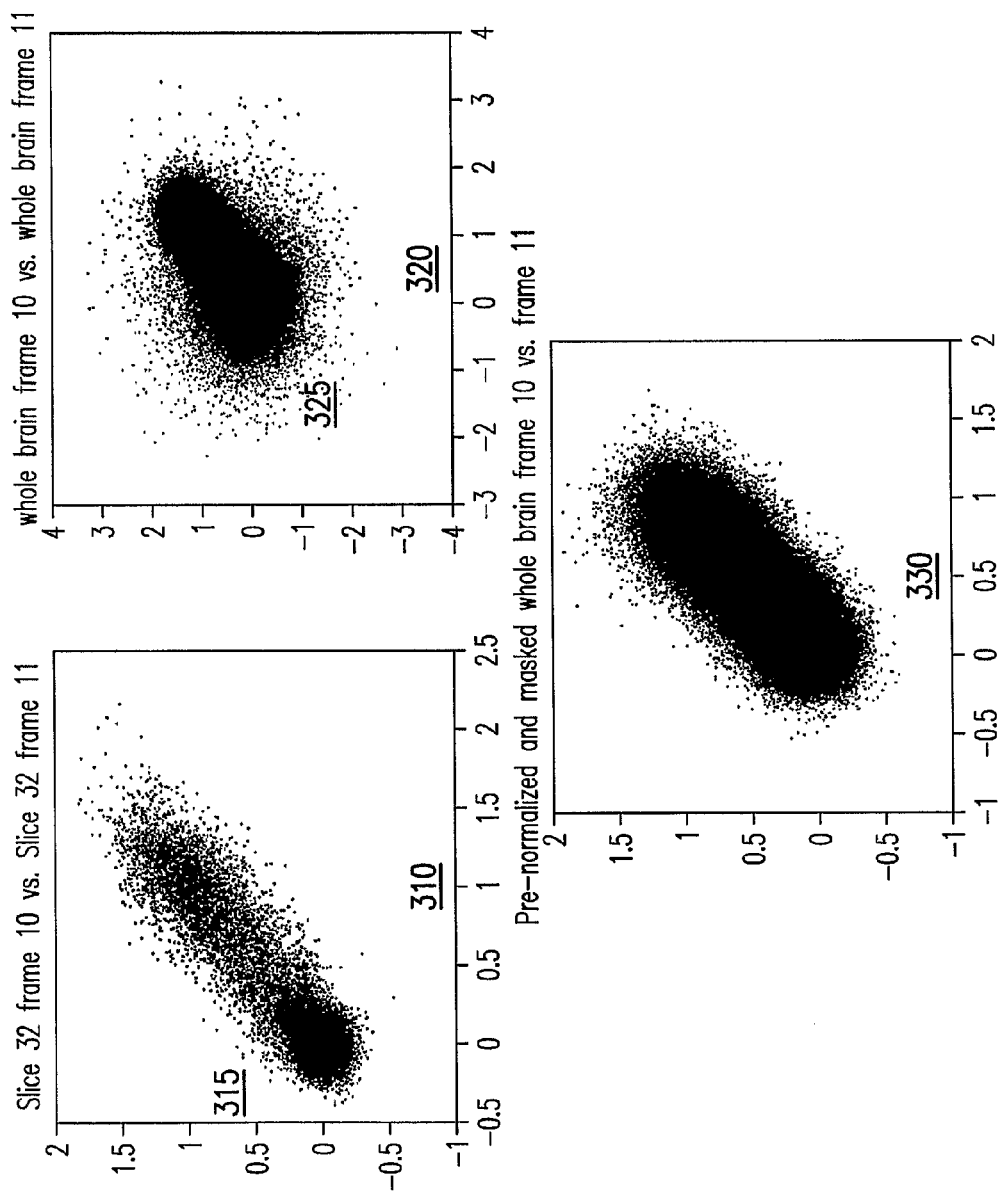
FIG. 3 is a graph illustrating a comparison between slice-wise (SW) and volume-wise (VW) approaches to performing PCA on dynamic PET images according to one embodiment of the present invention

FIG. 3 is a graph illustrating a comparison between slice-wise (SW) and volume-wise (VW) approaches to performing PCA on dynamic PET images according to one embodiment of the present invention. The data represent the value of the pixels in two different frames of an image where the image is either a slice 310 or whole volume (volume-wise) 320, 330 of the brain in an example PET study. A slice-wise approach without pre-normalization is illustrated in the first scatter plot diagram 310 where a high cluster of pixel values 315 around the zero (0,0) origin representing mostly background noise outside of the brain is shown for frames 10 and 11 of slice 32 in the example PET study. By comparison, using volume-wise (i.e., whole brain) dynamic PET input data without pre-normalization rather than SW data is shown in a second scatter plot diagram 320 where the cluster of pixels 325 around the zero (0,0) is still apparent but there is more even data distribution for frames 10 and 11. The volume-wise data shown in this scatter plot diagram 320 does not exclude the background data. Volume-wise (whole brain) data for frames 10 and 11 of the same example PET study that is masked to exclude the background data from the pre-normalized PET input data as described in FIG. 2 above is illustrated in a third scatter plot diagram 330 showing a homogenous data distribution without the clustering around the zero (0,0) origin due to background noise. It is important in improving the PCA to exclude this background noise near zero because it is otherwise included in the search for the maximum variance and tends to place the projection of the first principal component (the PC1 image) perpendicular to a line through the origin (0,0).

The PCA step 150 can be described in general as follows. The masked input data used in the masked volume-wise application of PCA (MVW-PCA) may be represented in a matrix X' composed of column vectors $X_i$ that contain the masked object pixel data (e.g., the brain data) for the different frames 1 to i. This matrix may be represented as follows:

$$X' = [X_1, X_2, X_3, \ldots, X_p]$$

where the matrix X' has an associated variance-covariance matrix S with eigenvalues $\lambda = [\lambda_1, \lambda_2, \lambda_3, \ldots, \lambda_p]$ and corresponding eigenvectors $e = [e_1, e_2, e_3, \ldots, e_p]$ where $\lambda_1 \geq \lambda_2 \geq \lambda_3 \geq \ldots \geq \lambda_p \geq 0$ and p corresponds to the number of the input column in the matrix X'. The $q^{th}$ principal component (PCq) may then be generated using the following equation where q=p:

$$Y_q = e'X = e_{q1}X_1 + e_{q2}X_2 + e_{q3}X_3 + \ldots + e_{qp}X_p$$

PCA using this equation requires uncorrelated components meaning that the condition $Cov(Y_q, Y_i) = 0$ where $i \neq q$ is necessary. In addition, each PC is orthogonal to all other PCs meaning that the first PC (e.g., PC1) represents the linear combination of the original variables (i.e., the masked input data) which contain (i.e., explains) the greatest amount of variance (maximum variance). The second PC (e.g., PC2) represents the combination of variables containing as much of the remaining variance as possible (i.e., defining the next largest amount of variance) orthogonal to the first PC (i.e., independent of the first principal component) and so on for the following PCs. Each PC explains the magnitude of variance in decreasing order. Performing PCA on the whole brain rather by slice allows the largest variance on all the structures of the reference object (e.g., the brain) to be determined for the first PC. This description of PCA is for one embodiment of the present invention and is included as a representative example of PCA. In other embodiments of the present invention, PCA may be performed differently and/or by using different equations other than those described herein.

Figure 4:
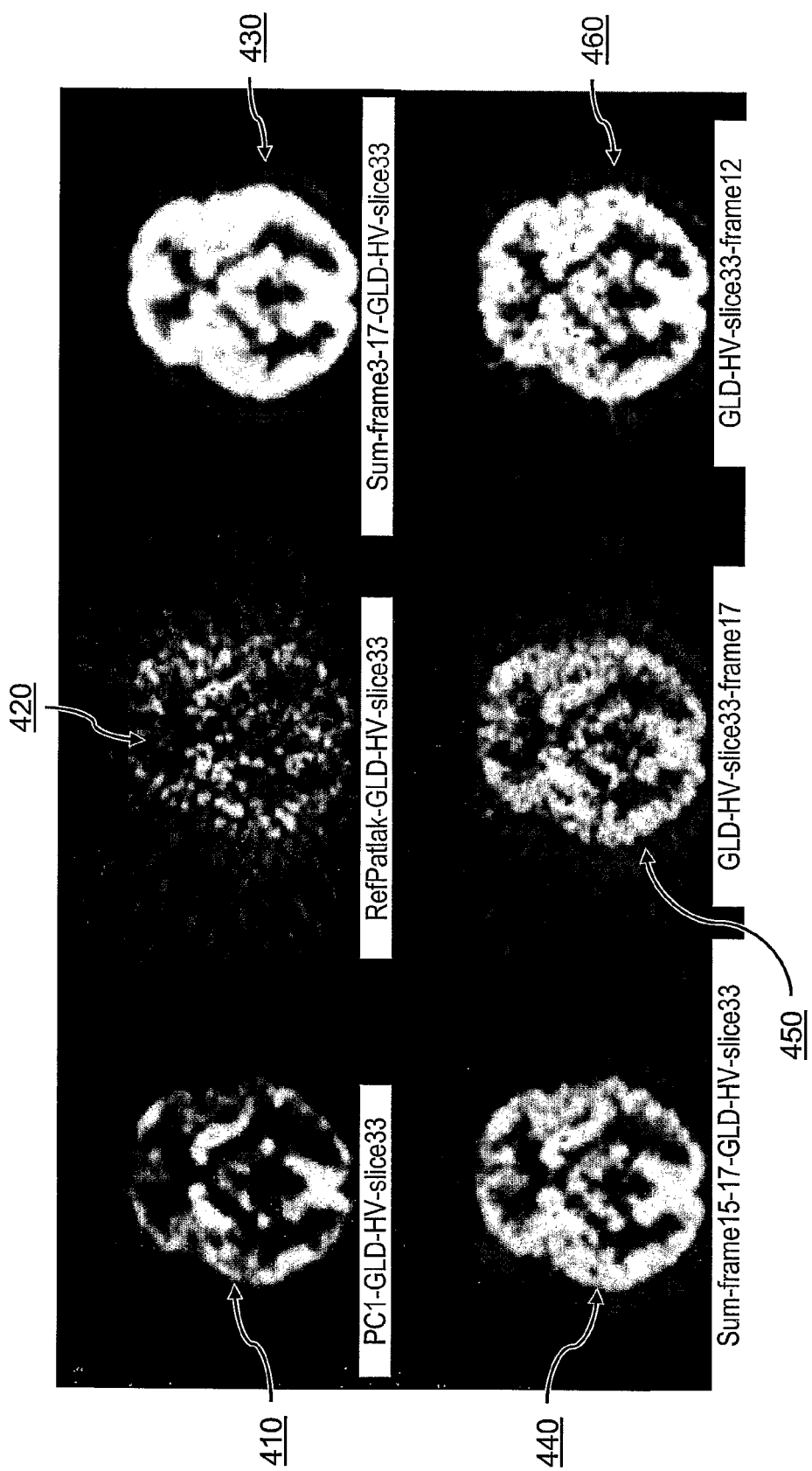
FIG. 4 is a comparative selection of PET images resulting from conventional dynamic PET image generation in relation to the first principal component (PC1 image) that results from applying PCA on dynamic PET images according to one embodiment of the present invention in a PET study of the human brain in a healthy volunteer using an $[^{11}C]$-GR205171 (GLD) tracer.

FIG. 4 is a comparative selection of PET images resulting from conventional dynamic PET image generation in relation to the first principal component (PC1 image) that results from applying PCA on dynamic PET images according to one embodiment of the present invention in a PET study of the human brain in a healthy volunteer using an $[^{11}C]$-GR205171 (GLD) tracer. The displayed images 410, 420, 430, 440, 450, 460 are taken for a particular plane (slice) of the PET study (slice 33 in this example) to allow a comparison between the methods and the original images using a GLD tracer. An image obtained using the available reference Patlak method 420 applied to input data from the frames 20-60 minutes into the PET study shows some improved discrimination between the regions with different levels of binding but the resulting image contains considerable noise. An image obtained using the available sum images method for frames 3-17 430 and an image obtained using the available sum images method for frames 15-17 440 both 430, 440 exhibit less noise than the reference Patlak image 420 but both 430, 440 have reduced discrimination between the regions with different levels of binding than shown in images obtained using MVW-PCA 410. These conventional methods 420, 430, 440 may be compared to see their various advantages and disadvantages in relation to the original image for slice 33 from frame 17 450 and the original image for slice 33 from frame 12 460. The first principal component image (PC1 image) 410 generated according to one embodiment of the present invention using a GLD tracer exhibits improved visualization quality and discrimination between the regions with different levels of binding while retaining a low noise level as compared with the other conventional methods 420, 430, 440 and original images 450, 460. The PC1 image 410 according to this embodiment captures the main features of the slice 33 images while other areas of different kinetic activity are captured in the higher components (e.g., PC2, PC3, etc.).

Figure 5:
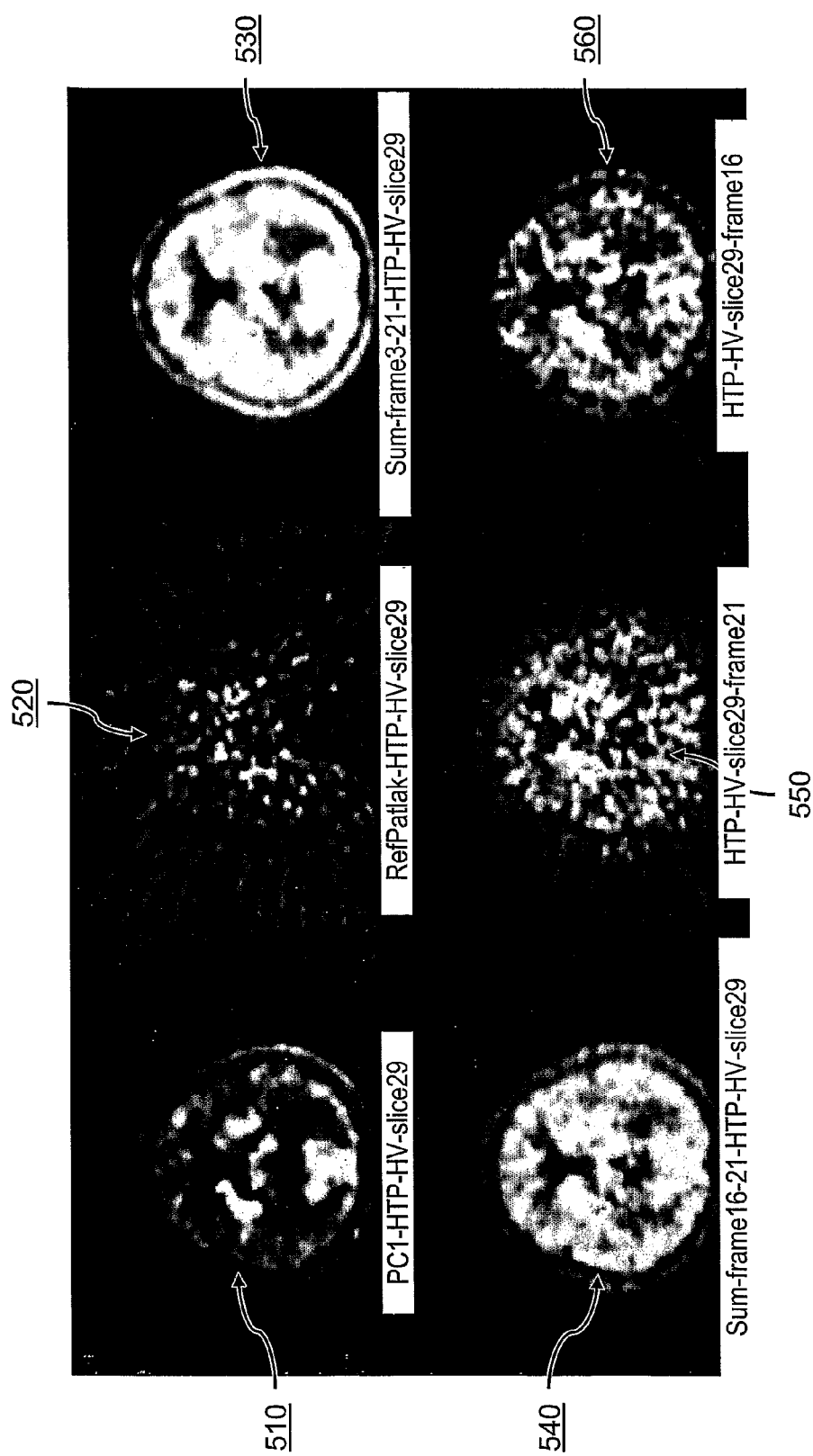
FIG. 5 is a comparative selection of PET images resulting from conventional dynamic PET image generation in relation to the first principal component (PC1 image) that results from applying PCA on dynamic PET images according to one embodiment of the present invention in a PET study of the human brain in a healthy volunteer using an $[^{11}C]$-5-Hydroxy-L-Tryptophan (HTP) tracer.

FIG. 5 is a comparative selection of PET images resulting from conventional dynamic PET image generation in relation to the first principal component (PC1 image) that results from applying PCA on dynamic PET images according to one embodiment of the present invention in a PET study of the human brain in a healthy volunteer using an $[^{11}C]$-5-Hydroxy-L-Tryptophan (HTP) tracer. The displayed images 510, 520, 530, 540, 550, 560 are taken for a particular plane (slice) of the PET study (slice 29 in this example) to allow a comparison between the methods and the original images using an HTP tracer. An image obtained using the available reference Patlak method 520 applied to input data from the frames 20-60 minutes into the PET study shows some improved discrimination between the regions with different levels of binding but the resulting image contains considerable noise. An image obtained using the available sum images method for frames 3-21 530 and an image obtained using the available sum images method for frames 16-21 540 both 530, 540 exhibit less noise than the reference Patlak image 520 but both 530, 540 have reduced discrimination between the regions with different levels of binding than shown in images obtained using MVW-PCA 510. These conventional methods 520, 530, 540 may be compared to see their various advantages and disadvantages in relation to the original image for slice 29 from frame 21 550 and the original image for slice 29 from frame 16 560. The first principal component image (PC1 image) 510 generated according to one embodiment of the present invention using an HTP tracer still exhibits improved visualization quality and discrimination between the regions with different levels of binding while retaining a low noise level as compared with the other conventional methods 520, 530, 540 and original images 550, 560. The PC1 image 510 according to this embodiment captures the main features of the slice 29 images while other areas of different kinetic activity are captured in the higher components (e.g., PC2, PC3, etc.).

Figure 6:
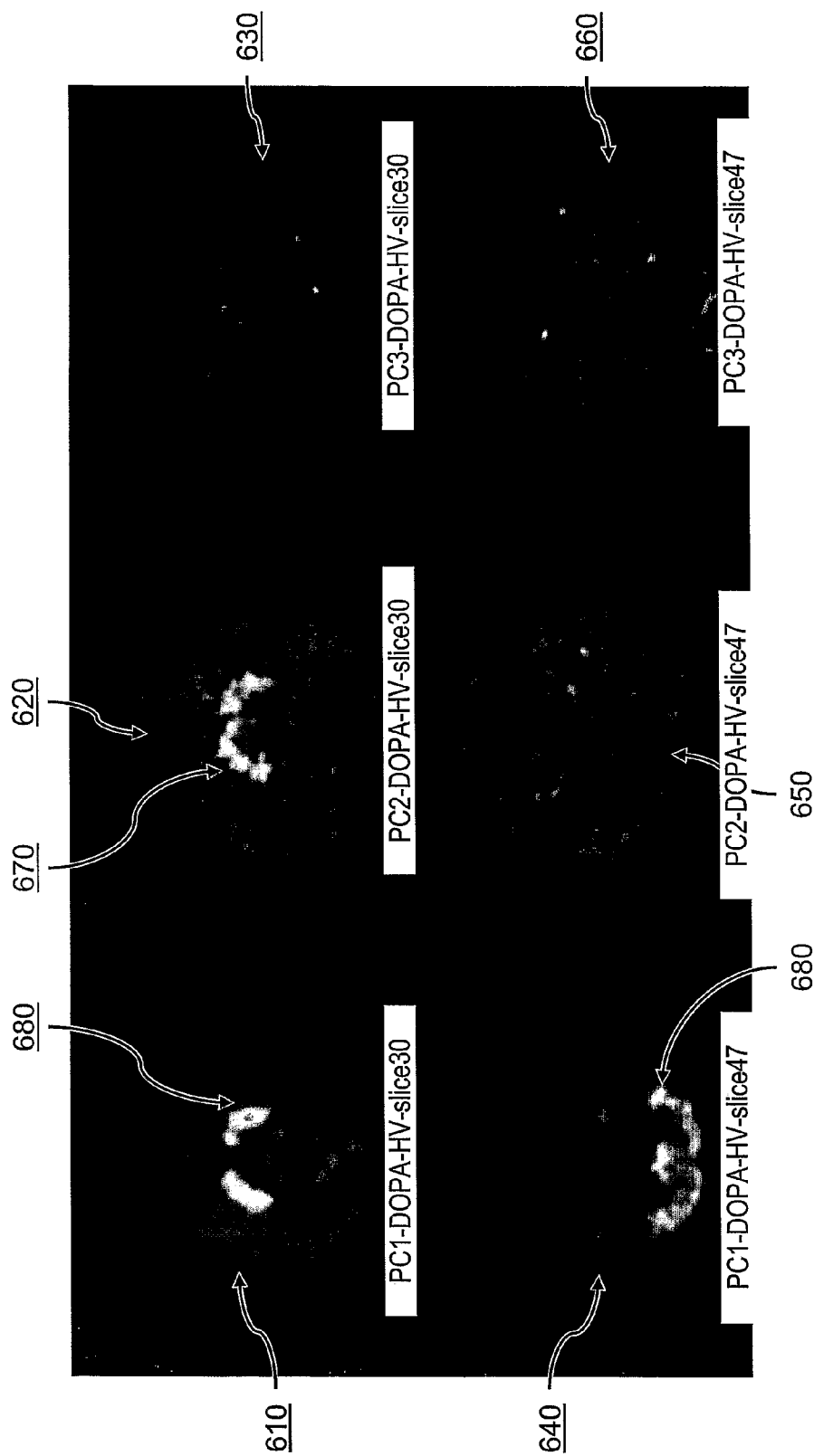
FIG. 6 is a selection of principal components (PC images) for two different levels of the brain (i.e., for two different slices) where PCA was applied on dynamic PET images according to one embodiment of the present invention in a PET study of the human brain in a healthy volunteer using an $[^{11}C]$-L-DOPA (DOPA) tracer.

FIG. 6 is a selection of principal components (PC images) for two different levels of the brain (i.e., for two different slices) where PCA was applied on dynamic PET images according to one embodiment of the present invention in a PET study of the human brain in a healthy volunteer using an [L$^{11}$C]-L-DOPA (DOPA) tracer. Three principal components for two slices or levels of the brain—slice 30 and slice 47—are displayed in FIG. 6. The main features of the kinetic activity are captured in the PC1 image of slice 30 610 and the PC1 image of slice 47 640 as shown by the discrimination between areas with different levels of DOPA tracer utilization. The PC2 image of slice 30 620 and the PC2 image of slice 47 650 show regions with different kinetic behavior compared to their respective PC1 images 610, 640. The PC2 image for slice 30 620 in particular shows notable kinetic activity 670 (e.g., striatum is visible). The main kinetic features 680 in the image sequence are captured in the first two principal components and therefore the PC3 image for slice 30 630 and the PC3 image for slice 47 660 contain mostly noise. FIG. 6 illustrates the differences in the kinetic activity shown in the different principal components resulting from applying a PCA analysis on the dynamic PET images according to one embodiment of the present invention.

Figure 7:
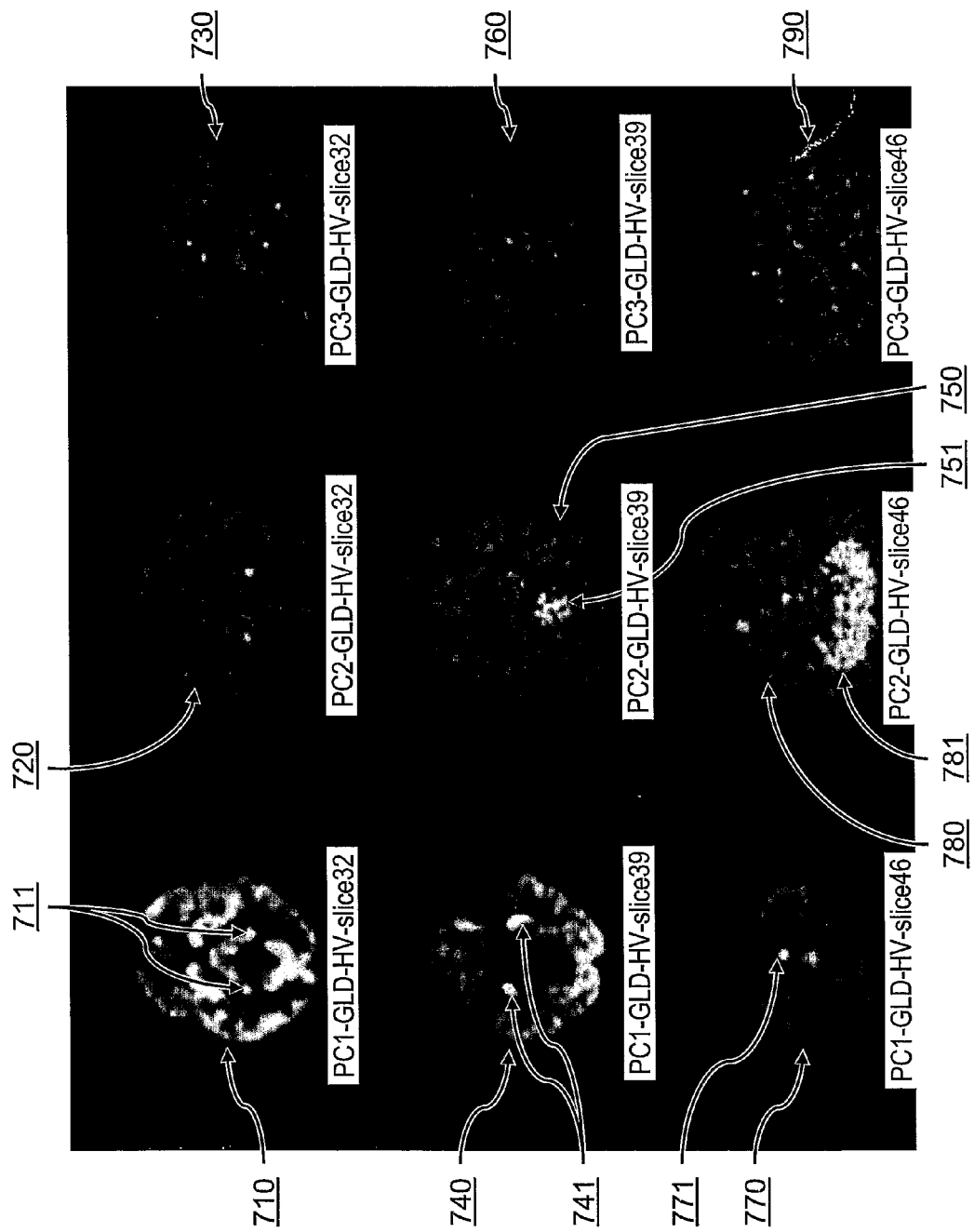
FIG. 7 is a selection of the principal components (PC1, PC2, and PC3 images) for three different levels of the brain (i.e., for three different slices) where PCA was applied on dynamic PET images according to one embodiment of the present invention in a PET study of the human brain in a healthy volunteer using an $[^{11}C]$-GR205171 (GLD) tracer.

FIG. 7 is a selection of the principal components (PC1, PC2, and PC3 images) for three different levels of the brain (i.e., for three different slices) where PCA was applied on dynamic PET images according to one embodiment of the present invention in a PET study of the human brain in a healthy volunteer using an [$^{11}$C]-GR205171 (GLD) tracer. Three principal components for three slices or levels of the brain—slices 32, 39, and 46—are displayed in FIG. 7. The results across the slices and the principal components show the differences in GLD tracer kinetic behavior through the discrimination between the different areas of the brain with different levels of tracer binding. The main features of the kinetic activity are captured in the PC1 image of slice 32 710, the PC1 image of slice 39 740, and the PC1 image of slice 46 770. The PC2 image of slice 32 720, the PC2 image of slice 39 750, and the PC2 image of slice 46 780 show regions with different kinetic behavior compared to their respective PC1 images 710, 740, 770. The PC2 images for slice 39 750 and slice 46 780 in particular show notable kinetic activity. The main kinetic features in the image sequence are captured in the first two principal components and therefore the PC3 images for slice 32 730, slice 39 760, slice 46 790 contain mostly noise. The PC images shown in FIG. 7 obtained according to one embodiment of the present invention indicate the differences in kinetic activity (behavior) in small structures in the brain which other conventional methods could not visualize such as, for example, the caudate nucleus and putamen 711 shown in the PC1 image of slice 32 710, the hippocampus 741 shown in the PC1 image of slice 39 740, and the pituitary 771 shown in the PC1 image of slice 46 770. Additional example include the pons 751 which is visible in the PC2 image of slice 39 750 and the cerebellum 781 is visible in the PC2 image of slice 49 780 indicating their different kinetic behavior compared with the main aspects of the brain.

FIG. 8*a* is a selection of first principal component images taken from different perspectives or planes generated by applying the MVW-PCA method on dynamic PET images according to one embodiment of the present invention in a PET study of the human brain in a healthy volunteer using a Pittsburgh Compound-B (PIB) tracer. FIG. 8*b* is a selection of first principal component images taken from different perspectives or planes generated by applying the MVW-PCA method on dynamic PET images according to one embodiment of the present invention in a PET study of the human brain in a patient with Alzheimer's disease using a Pittsburgh Compound-B (PIB) tracer. The PC1 images are shown from a coronal 810, 850, transaxial 820, 860, and sagittal 830, 870 perspective. FIGS. 8*a* and 8*b* show a good discrimination between regions with different amyloid binding in the brain of an Alzheimer's disease patient as compared to a healthy volunteer obtained by using one embodiment of the MVW-PCA method. The Alzheimer's disease patient shows dominant PIB tracer binding in the frontal cortex 881 compared to a healthy volunteer 841 and in the lateral and posterior aspects of the temporal lobes 882 compared to a healthy volunteer 842.

FIG. 9*a* is a selection of first principal component images taken from different perspectives or planes generated by applying the MVW-PCA method on dynamic PET images according to one embodiment of the present invention in a PET study of the human brain in a healthy volunteer using an [$^{11}$C]-L-deuterium-deprenyl (DED) tracer. FIG. 9*b* is a selection of first principal component images taken from different perspectives or planes generated by applying the MVW-PCA method on dynamic PET images according to one embodiment of the present invention in a PET study of the human brain in a patient with Alzheimer's disease using an [$^{11}$C]-L-deuterium-deprenyl (DED) tracer. The PC1 images are shown from a coronal 910, 950, transaxial 920, 960, and sagittal 930, 970 perspective. FIGS. 9*a* and 9*b* show good differences in the uptake of DED in different regions of the brain of an Alzheimer's disease patient as compared to a healthy volunteer obtained by using one embodiment of the MVW-PCA method. The Alzheimer's disease patient shows increased DED tracer binding especially in the frontal cortex 981 compared to a healthy volunteer 941 and in the medial aspects of the parietal cortex 982 compared to a healthy volunteer 942.

Figure 10A:
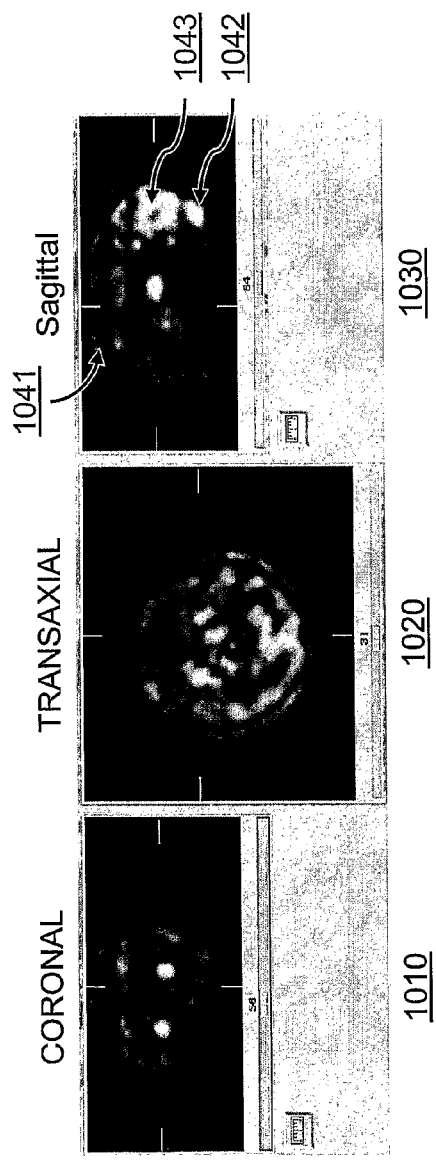
FIG. 10a is a selection of first principal component images taken from different perspectives or planes generated by applying the MVW-PCA method on dynamic PET images according to one embodiment of the present invention in a PET study of the human brain in a healthy volunteer using an $[^{11}C]$-5-Hydroxy-L-Tryptophan (HTP) tracer.
Figure 10B:
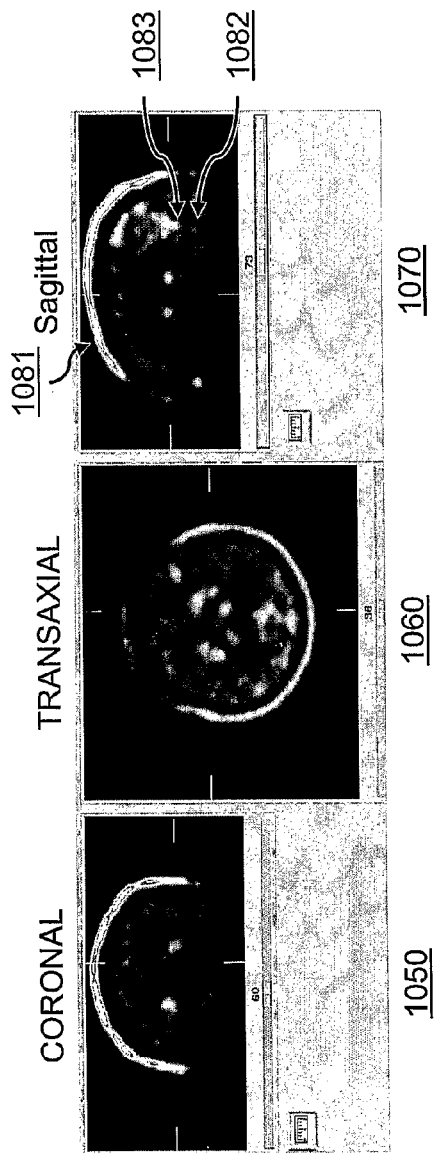
FIG. 10b is a selection of first principal component images taken from different perspectives or planes generated by applying the MVW-PCA method on dynamic PET images according to one embodiment of the present invention in a PET study of the human brain in a patient with chronic fatigue syndrome (CFS) using an $[^{11}C]$-5-Hydroxy-L-Tryptophan (HTP) tracer.

FIG. 10*a* is a selection of first principal component images taken from different perspectives or planes generated by applying the MVW-PCA method on dynamic PET images according to one embodiment of the present invention in a PET study of the human brain in a healthy volunteer using an [$^{11}$C]-5-Hydroxy-L-Tryptophan (HTP) tracer. FIG. 10*b* is a selection of first principal component images taken from different perspectives or planes generated by applying the MVW-PCA method on dynamic PET images according to one embodiment of the present invention in a PET study of the human brain in a patient with chronic fatigue syndrome (CFS) using an [$^{11}$C]-5-Hydroxy-L-Tryptophan (HTP) tracer. The PC1 images are shown from a coronal 1010, 1050, transaxial 1020, 1060, and sagittal 1030, 1070 perspective. FIGS. 10*a* and 10*b* show clear differences in the uptake of HTP in different regions of the brain of a chronic fatigue syndrome (CFS) patient as compared to a healthy volunteer obtained by using one embodiment of the MVW-PCA method. The predominant feature in these figures is the very high uptake of the HTP tracer in the extracranial soft tissues 1081 of the CFS patient compared to a healthy volunteer 1041 and the redistribution of the HTP tracer within the brain of the CFS patient including the reduction of HTP tracer uptake in the cerebellum 1082 and the occipital lobe 1083 compared to the healthy volunteer 1042, 1043.

FIG. 11a is a selection of first principal component images taken from different perspectives or planes generated by applying the MVW-PCA method on dynamic PET images according to one embodiment of the present invention in a PET study of the human brain in a healthy volunteer using an [$^{11}$C]-L-DOPA (DOPA) tracer. FIG. 11b is a selection of first principal component images taken from different perspectives or planes generated by applying the MVW-PCA method on dynamic PET images according to one embodiment of the present invention in a PET study of the human brain in a patient with chronic fatigue syndrome (CFS) using an [$^{11}$C]-L-DOPA (DOPA) tracer. The PC1 images are shown from a coronal 1110, 1150, transaxial 1120, 1160, and sagittal 1130, 1170 perspective. FIGS. 11a and 11b show clear differences in the uptake of the DOPA tracer in different regions of the brain of a CFS patient as compared to a healthy volunteer obtained by using one embodiment of the MVW-PCA method. The results are similar to FIGS. 10a and 10b showing HTP tracer uptake except that predominant feature in FIGS. 11a and 11b is only in the extracranial soft tissues 1081 of the CFS patient compared to a healthy volunteer 1041.

FIG. 12 is a block diagram illustrating the platform on which the MVW-PCA method for applying PCA to dynamic PET images using pre-normalization techniques may operate according to one embodiment of the present invention. Functionality of the foregoing embodiments may be provided on various computer platforms executing program instructions. One such platform 1200 is illustrated in the simplified block diagram of FIG. 12. There, the platform 1200 is shown as being populated by a processor 1210, a memory system 1220 and an input/output (I/O) unit 1230. The processor 1210 may be any of a plurality of conventional processing systems, including microprocessors, digital signal processors and field programmable logic arrays. In some applications, it may be advantageous to provide multiple processors (not shown) in the platform 1200. The processor(s) 1210 execute program instructions stored in the memory system. The memory system 1220 may include any combination of conventional memory circuits, including electrical, magnetic or optical memory systems. As shown in FIG. 12, the memory system may include read only memories 1222, random access memories 1224 and bulk storage 1226. The memory system not only stores the program instructions representing the various methods described herein but also can store the data items on which these methods operate. The I/O unit 1230 would permit communication with external devices (not shown).

What is claimed is:

1. A method of volume-wise positron emission tomography image analysis of dynamic positron emission tomography images including a background and an object to study, the images comprising multiple frames of multiple slices, the method, comprising the steps of:
    (a) masking the background in the dynamic positron emission tomography images, said masking comprising the steps of:
        (i) generating a first principal component image as a function of applying a principal component analysis method on the positron emission tomography images for the positron emission tomography image;
        (ii) determining a threshold value for the first principal component image image;
        (iii) converting the first principal component image into a binary image as a function of the threshold value wherein each pixel in the first principal component image is assigned a binary value indicating whether it is one of an object pixel and a background pixel;
        (iv) identifying a set of coordinates for the object pixels wherein the set of coordinates identifies the object pixels in the dynamic positron emission tomography image;
        (v) extracting an object pixel value from the dynamic positron emission tomography image as a function of the set of coordinates for the object pixel; and
        (vi) storing the object pixel value in a column vector of a matrix; and
    (b) performing pre-normalization on the masked dynamic positron emission tomography images from step (A), said pre-normalization comprising the steps of:
        (i) normalizing the masked dynamic positron emission tomography images to correct for a background noise;
        (ii) performing a kinetic pre-normalization by determining a region of interest for an outlined region of the object under study in the masked positron emission tomography images;
        (iii) dividing all f the slices for each frame by the mean value within the region of interest within the frame; and
    applying a multivariate analysis method on the masked pre-normalized dynamic positron emission tomography images.

2. The method according to claim 1, the normalizing step further comprising:
    dividing each pixel of the masked dynamic positronemission tomography images by a standard deviation of the background noise.

3. The method according to claim 1, wherein the pre-normalization step represents a reference region is determined as a function of outlining at least one region of interest for a biological/anatomical area being studied in the positron emission tomography image.

4. The method according to claim 1, wherein the region of interest represents a reference region that is devoid of specific binding with a radioactive.

5. The method according to claim 1, wherein the multivariate analysis method of the applying step is a principal component analysis method.

6. The method according to claim 1, the determining step further comprising:
    determining a threshold value for the set of dynamic PET images using the Otsu method.

7. The method according to claim 1, further comprising:
    storing the set of coordinates for the object pixel in a second column vector of a second matrix.

8. The method according to claim 1, the determining step further comprising:
    determining a threshold value for the set of dynamic PET images using the Otsu method.

9. The method according to claim 1, further comprising:
    storing the set of coordinates for the object pixel in a second column vector of a second matrix.

10. A system for improving quality in a positron emission tomography image, comprising:
    a memory system;
    an input/output unit; and
    a processor, wherein the processor is adapted to perform the method of claim 1.

11. A method for creating a masked input data set masking a background in positron emission tomography images including a background and an object to study, the images comprising multiple frames of multiple slices, comprising the steps of:
  generating a first principal component image as a function of applying a principal component analysis method on the dynamic PET images;
  determining a threshold value for the first principal component image;
  converting the first principal component image into a binary image as a function of the threshold value wherein each pixel in the first principal component image is assigned a binary value indicating whether it is at least one of an object pixel and a background pixel;
  identifying a set of coordinates for the object pixels wherein the set of coordinates identifies the object pixels in the positron emission tomography image;
  extracting an object pixel value from the positron emission tomography image as a function of the set of coordinates for the object pixel; and
  storing the object pixel value in a column vector of a matrix.

12. A computer readable medium including instructions adapted to execute a method for improving quality in a positron emission tomography image, the method comprising:
  creating a masked input data set masking a background in a positron emission tomography image, the method comprising:
    generating a first principal component image as a function of applying a multivariate analysis method on a set of dynamic PET images for the positron emission tomography image;
    determining a threshold value for the set of dynamic PET images;
    converting the first principal component image into a binary image as a function of the threshold value wherein a pixel in the first principal component image is assigned a binary value indicating whether it is at least one of an object pixel and a background pixel;
    identifying a set of coordinates for the object pixel wherein the set of coordinates identifies the object pixel in the positron emission tomography image;
    extracting an object pixel value from the positron emission tomography image as a function of the set of coordinates for the object pixel; and
    storing the object pixel value in a column vector of a matrix;
  masking a background in the positron emission tomography image, wherein masking generates a new set of input data for the positron emission tomography image;
  normalizing a pixel in the new set of input data for the positron emission tomography image to correct for a background noise;
  determining a reference region in the positron emission tomography image;
  enhancing a contrast of the pixel in the new set of input data for the positron emission tomography image as a function of the reference region; and
  applying a multivariate analysis method on the new set of input data for the positron emission tomography image.

* * * * *